US012590984B2

(12) United States Patent　　　(10) Patent No.:　US 12,590,984 B2

Wedl et al.　　　(45) Date of Patent:　Mar. 31, 2026

(54) METHOD FOR DETERMINING AT LEAST ONE SPEED COMPONENT OF A FLUID STREAM

(71) Applicant: TECHNISCHE UNIVERSITÄT WIEN, Vienna (AT)

(72) Inventors: Günter Wedl, Vienna (AT); Christian Jordan, Mistelbach (AT); Bahram Haddadi, Vienna (AT); Michael Harasek, Vienna (AT)

(73) Assignee: TECHNISCHE UNIVERSITAT WIEN, Vienna (AT)

( * ) Notice: Subject to any disclaimer, the term of this patent is extended or adjusted under 35 U.S.C. 154(b) by 187 days.

(21) Appl. No.: 18/261,798

(22) PCT Filed: Jan. 19, 2022

(86) PCT No.: PCT/AT2022/060013

§ 371 (c)(1),
(2) Date: Jul. 17, 2023

(87) PCT Pub. No.: WO2022/155692

PCT Pub. Date: Jul. 28, 2022

(65) Prior Publication Data

US 2024/0069060 A1　　Feb. 29, 2024

(30) Foreign Application Priority Data

Jan. 19, 2021　(AT) ............................... A 50019/2021

(51) Int. Cl.
*G01N 21/39*　　(2006.01)
*G01P 5/26*　　(2006.01)
(Continued)

(52) U.S. Cl.
CPC ................ *G01P 5/26* (2013.01); *A61B 8/488* (2013.01); *A61H 2230/25* (2013.01); *G01J 3/44* (2013.01);
(Continued)

(58) Field of Classification Search
CPC ....... G01P 5/26; A61B 8/488; A61H 2230/25; G01J 3/44; G01N 2021/392; G01N 2021/4709; G01N 21/65; G01S 17/58
See application file for complete search history.

(56) References Cited

U.S. PATENT DOCUMENTS 3,547,540 A * 12/1970 Shigemoto .............. G01S 17/50
356/28
4,669,876 A 6/1987 Dopheide
(Continued)

FOREIGN PATENT DOCUMENTS

AT　　　520087 A4　　1/2019
DE　　39 37 851 A1　　5/1990
(Continued)

OTHER PUBLICATIONS

International Search Report issued in corresponding application, PCT/AT2022/060013; mailing date: Apr. 19, 2022.
(Continued)

*Primary Examiner* — Michelle M Iacoletti
*Assistant Examiner* — Judy Dao Tran
(74) *Attorney, Agent, or Firm* — Chrisman Gallo Tochtrop LLC

(57) ABSTRACT

The application relates to a method for determining at least one speed component of a fluid stream, in particular for laser Doppler anemometry, the method having at least the steps of: —providing at least a first part-beam and a second part-beam; —directing the first part-beam along a first optical path and directing the second part-beam along a
(Continued)

second optical path onto a superimposition region within the fluid stream so that the first optical path and the second optical path intersect in the superimposition region; —detecting a Doppler-shifted first part-beam scattered light signal, which was back-scattered by tracer particles in the fluid stream in the superimposition region, at least partially following the first optical path; —detecting a Doppler-shifted solid angle scattered light signal, which was scattered by the tracer particles in the superimposition region into a path different at least from the first optical path and from the second optical path. The application also relates to a corresponding device.

22 Claims, 6 Drawing Sheets

(51) Int. Cl.

| | | |
|---|---|---|
| *A61B 8/00* | (2006.01) | |
| *G01J 3/44* | (2006.01) | |
| *G01N 21/47* | (2006.01) | |

(52) U.S. Cl.

CPC ................. *G01N 2021/392* (2013.01); *G01N 2021/4709* (2013.01)

(56) References Cited

U.S. PATENT DOCUMENTS

| 4,990,971 | A | | 2/1991 | Nishi | |
|---|---|---|---|---|---|
| 4,997,272 | A | | 3/1991 | Dopheide et al. | |
| 6,261,233 | B1 | * | 7/2001 | Kantorovich | A61B 8/06 |
| | | | | | 600/454 |
| 8,077,294 | B1 | * | 12/2011 | Grund | G01N 21/65 |
| | | | | | 356/3.01 |
| 2019/0285753 | A1 | * | 9/2019 | Spruit | G01S 7/497 |
| 2020/0150045 | A1 | | 5/2020 | Harasak et al. | |
| 2020/0200577 | A1 | | 6/2020 | Van Der Lee et al. | |
| 2020/0319082 | A1 | * | 10/2020 | Mutlu | G01P 5/001 |
| 2023/0026894 | A1 | * | 1/2023 | Misawa | G02B 21/0064 |

FOREIGN PATENT DOCUMENTS

| DE | 10 2005 042 954 | A1 | | 3/2007 | | |
|---|---|---|---|---|---|---|
| DE | 10 2018 222 590 | A1 | | 6/2020 | | |
| EP | 0 333 905 | A1 | | 9/1989 | | |
| EP | 0 152 916 | B1 | | 12/1991 | | |
| GB | 2 213 018 | B | | 8/1989 | | |
| WO | 2010/058322 | A1 | | 5/2010 | | |
| WO | WO-2018192996 | A1 | * | 10/2018 | | G01J 3/44 |

OTHER PUBLICATIONS

Written Opinion issued in corresponding application, PCT/AT2022/060013; mailing date: Apr. 19, 2022.

Austrian Office Action issued in corresponding application, A 50019/2021; issued Nov. 15, 2021.

International Preliminary Report on Patentability and Written Opinion issued in corresponding application, PCT/AT2022/060013, dated Jul. 20, 2023.

* cited by examiner

1

METHOD FOR DETERMINING AT LEAST ONE SPEED COMPONENT OF A FLUID STREAM

CROSS-REFERENCE TO RELATED APPLICATIONS

This application is a U.S. National Stage entry of PCT/AT2022/060013, filed Jan. 19, 2022, which claims benefit of priority to Austrian application A-50019/2021, filed Jan. 19, 2021, the entire disclosures of which are hereby incorporated herein by reference.

FIELD OF THE INVENTION

The invention relates to a method for determining at least one speed component of a fluid stream, in particular a method for laser Doppler anemometry. The invention also relates to a device for determining at least one speed component of a fluid stream, in particular a device for laser Doppler anemometry or a laser Doppler anemometer.

BACKGROUND OF THE INVENTION

The characterisation of process streams, in particular 3-dimensional characterisation, is of great importance for industry, medicine and in laboratories. An important non-contact optical measurement method for determining speed components in fluid streams is laser Doppler anemometry (LDA; also: laser Doppler velocimetry, LDV). This is based on the determination of the Doppler shift of the frequency of the irradiated light that impinges on a moving object. Single-beam laser Doppler systems, dual-beam laser Doppler systems, and multi-beam laser Doppler systems are known. In the two-beam laser Doppler system, two excitation beams are crossed in a measuring volume, and the resulting Doppler-shifted scattered light is detected and evaluated. In order to detect more than one speed component, more than one beam pair can be used. However, this requires several different laser wavelengths or a frequency manipulation with, for example, a Bragg cell. This makes complex systems necessary. Furthermore, several sensors distributed in space can be provided, in which case several measuring holes are necessary. Furthermore, some systems require a polariser.

GB 2 213 018 B shows an LDA for 3D speed measurement based on polarisation angle measurement. Here, a laser beam is directed via an output module onto a beam splitter. The two beams converge onto a measurement volume. Means are provided to adjust the position of the output module and of the beam splitter in order to, in turn, adjust the position to which the two beams converge. Scattered light is received via a spatially offset receiving window and fed to a photoelectron multiplier. Reference measurements are necessary to determine the speed components.

DE 39 37 851 A1 shows an LDA method in which measurement is carried out using an ultrasonic light deflector serving as a frequency shifter.

Furthermore, AT 520087 A4 shows a combination of an LDA with a Raman spectrometer.

However, the methods known in the prior art do not allow the complete characterisation of at least one speed component to be determined in a constructively simple manner or without prior calibration or comparative measurements.

BRIEF SUMMARY OF THE INVENTION

The object of the present invention is to alleviate or avoid at least individual disadvantages of the prior art. In particular, it is an object of the present invention to enable the absolute value of a speed component of a stream to be determined in a simple manner and/or to improve the accuracy of a corresponding measurement.

This object is achieved by a method for determining at least one speed component of a fluid stream, in particular for laser Doppler anemometry, the method having at least the steps of:

providing at least a first part-beam and a second part-beam;

directing the first part-beam along a first optical path and directing the second part-beam along a second optical path onto a superimposition region within the fluid stream so that the first optical path and the second optical path intersect in the superimposition region;

detecting a Doppler-shifted first part-beam scattered light signal, which was back-scattered by tracer particles in the fluid stream in the superimposition region, at least partially following the first optical path;

detecting a Doppler-shifted solid angle scattered light signal, which was scattered by the tracer particles in the superimposition region into a path different at least from the first optical path and from the second optical path.

Furthermore, the problem is solved by a device for determining at least one speed component of a fluid stream, in particular for laser Doppler anemometry, the device comprising:

a light source arrangement for providing at least a first and a second part-beam;

an optical directing device for directing the first part-beam along a first optical path and the second part-beam along a second optical path to a superimposition region within a fluid stream so that the first optical path and the second optical path intersect in the superimposition region;

a (first) part-beam detector arranged to detect a Doppler-shifted first part-beam scattered light signal, which was back-scattered by tracer particles in the fluid stream in the superimposition region, at least partially following the first optical path;

a solid angle detector (or solid angle scattered light detector) arranged to detect a Doppler-shifted solid angle scattered light signal, which was scattered by the tracer particles in the superimposition region into a path different at least from the first optical path and from the second optical path.

The solid angle scattered light signal comprises a speed-dependent, characteristic Doppler frequency, which is dependent on the angle between the part-beams or on the angle between the part-beams and the measured object (i.e. the tracer particles). By detecting the solid angle scattered light signal, in particular the frequency of the solid angle scattered light signal, the total speed of the tracer particles and thus of the stream can be determined. The part-beam scattered light signals also comprise speed-dependent, characteristic Doppler frequencies that are directly proportional to the speed of the particles in the respective beam axis and are dependent on the total speed of the stream via the angles of movement of the tracer particles relative to the respective beam axis. Thus, by detecting both the solid angle scattered light signal and the first part-beam scattered light signal, at least the absolute value of a speed component of the tracer particles or of the stream in the superimposition region can be determined. Similarly, the absolute value of a speed component can be determined with the first part-beam detector and the solid angle detector. In particular, no frequency shift, no additional measuring holes and no reference measurements are necessary for this. Furthermore, by detecting the Doppler-shifted solid angle scatter signal and the first Doppler-shifted part-beam scatter signal (and preferably further Doppler-shifted part-beam scatter signals), redundancy and thus improved accuracy can be achieved. Furthermore, the direction of the movement can also be determined without frequency shift.

Tracer particles in the fluid stream are, for example, solid particles, liquid droplets and gas bubbles.

The first and second part-beams preferably comprise the same frequency and/or are coherent, in particular when incident on the superimposition region. Preferably, providing at least a first part-beam and a second part-beam comprises: providing a light beam; and/or splitting the light beam into at least the first part-beam and the second part-beam, in particular using a first beam splitter. Similarly, the light source arrangement preferably comprises a light source for providing a light beam and/or a first beam splitter for splitting the light beam into the first part-beam and the second part-beam. The light source is preferably a coherent light source, in particular a laser. In particular, the first optical path and the second optical path each extend from the first beam splitter to the superimposition region. Preferably, the first optical path and the second optical path are different outside the superimposition region.

The fluid stream is in particular a liquid stream and/or a gas stream and/or a particle stream. In particular, the speed component of the fluid stream is determined in the superimposition region, which represents a measurement volume or a focal point. In particular, the first optical path is partially different from the second optical path. The first part-beam and the second part-beam form an angle between each other when they enter the superimposition volume.

In particular, a filter may be provided to separate the respective Doppler-shifted component from the remaining scattered light, especially to separate the Doppler-shifted portion from the remaining scattered light (an analysis scattered light) of the solid angle scattered light signal. The solid angle detector and/or the first part-beam detector can be a photomultiplier, a photodiode or another sensor suitable for frequency measurement and/or wavelength measurement.

Preferably, the solid angle scattered light signal is a scattered light signal back-scattered by the tracer particles in the superimposition region into the path different from the first and second optical paths. In particular, the solid angle scattered light signal scattered into the path different from the first and second paths is scattered into a space different from the first and second paths. The method preferably comprises the step of: adding tracer particles to the fluid stream, if necessary. The path of the solid angle scattered light signal preferably lies at least partially between the first and second optical paths when they meet the superimposition region.

Preferably, the device is set up to carry out the method according to the invention, for which purpose in particular a control and data acquisition unit may be provided.

It is preferred if the method further comprises:
determining a first (part-)speed component (in particular a first relative speed component) of the fluid stream in the superimposition region from the first part-beam scattered light signal (in particular in the beam direction of the first part-beam);

determining a total speed (in particular an absolute total speed) of the fluid stream in the superimposition region from the Doppler-shifted solid angle scattered light signal;
determining a first direction of movement of the first speed component of the fluid stream in the superimposition region from the first speed component and the total speed.

The total speed V can be calculated, for example, from the measured frequency fa of the Doppler-shifted solid angle scattered light signal using formula 1

$$V = \frac{f_d \lambda}{2 \sin \theta_s} \tag{1}$$

wherein $\theta_s$ is the angle between the first and the second part-beam (more generally also: between the first and the third part-beam or the second and the third part-beam, see below) and $\lambda$ is the wavelength of the first and the second part-beam. The speed component $v_i$ (i=1, 2, 3) in the beam axis of the i-th part-beam can be calculated, for example, from the measured frequency $f_i$ (i=1, 2, 3) of the Doppler-shifted i-th part-beam scattered light signal using formula (2)

$$v_i = \frac{f_i \lambda}{2} = V \cos \theta_i \tag{2}$$

wherein $\lambda$ is the wavelength of the i-th part-beam and $\theta_i$ is the angle between the beam axis of the i-th part-beam and a coordinate axis of the fluid stream, in particular of the flow channel. The directional angle $\theta_i$ of the part-speed $$\theta_i = \cos^{-1} \frac{f_i \lambda}{2V} \tag{3}$$

is calculated (see formula (3)) from the total speed and the measured frequency $f_i$ of the part-beam scattered light signal.

It is advantageous if the method further comprises:
detecting a Doppler-shifted second part-beam scattered light signal, which was back-scattered by the tracer particles in the superimposition region, at least partially following the second optical path;
optionally determining a second (part-)speed component of the fluid stream in the superimposition region from the second part-beam scattered light signal;
optionally determining a second direction of movement of the second speed component of the fluid stream in the superimposition region from the second speed component and the total speed component.

Thus, it is also possible to determine a second speed component. The variants described in conjunction with the Doppler-shifted first part-beam scattered light signal can also be provided for the second part-beam scattered light signal.

It is preferred if the first part-beam scattered light signal and the second part-beam scattered light signal are detected by (at least) the same detector. In particular, the detector can detect light in the beam path of the light beam before the light beam is split into the first and second part-beams. In particular, the first beam splitter is provided as a detector beam splitter that guides the first and the second Doppler-shifted part-beam scattered light signals to the detector. It may also be provided that the first beam splitter guides the first and the second Doppler-shifted part-beam scattered light signals to the detector. Thus, all part-beam scattered light signals can be detected with a single detector.

In a preferred embodiment, the first part-beam scattered light signal and preferably the second part-beam scattered light signal is detected using the self-mixing effect, i.e. by means of self-mixing interferometry. In particular, the first part-beam scattered light signal and preferably the second part-beam scattered light signal is fed back into the light source, in particular a laser cavity of the light source, wherein it interferes with the internal optical field of the light source, and is detected. The detection can take place in the light source and/or at an aperture of the light source, the aperture facing away from the exit aperture for the light beam. Preferably, the light source is a laser with an open laser cavity.

It is advantageous if the first part-beam scattered light signal is led off from the first optical path for detection and is detected by a first part-beam detector and preferably the second part-beam scattered light signal is led off from the second optical path for detection and is detected by a second part-beam detector. Thus, the first part-beam scattered light signal and the second part-beam scattered light signal can be detected in a simple manner, or a distinction between the two signals is easily possible. For this purpose, detector beam splitters can be provided in the respective optical path and lead the respective part-beam scattered light signal away from the respective optical path for detection.

It is preferred if the first part-beam and the second part-beam are focused on the superimposition region with an optical element (so that the first optical path and the second optical path intersect in the superimposition region) and the Doppler-shifted solid angle scattered light signal is collimated with the same optical element. Thus, it is possible to achieve both the emission of the part-beams and the reception of the scattered light signals with only one optical element. The optical element is preferably a minor, in particular a concave minor. Thus, for example, the first and the second part-beams can be focused on the superimposition region from a section in which they are substantially collinear, while the solid angle scattered light signal scattered in the path different from the first and second optical paths is collimated by the optical element.

In a preferred variant, the detection of the Doppler-shifted first part-beam scattered light signal and optionally the detection of the Doppler-shifted second part-beam scattered light signal and/or the Doppler-shifted second part-beam scattered light signal comprises at least measuring the frequency of the respective scattered light signal.

In an advantageous variant, the method further comprises:
interrupting the second part-beam during detection of the Doppler-shifted first part-beam scattered light signal;
optionally interrupting the first part-beam during detection of the Doppler-shifted second part-beam scattered light signal.

This ensures that only the frequency corresponding to the respective part-beam is detected, the information obtained can be assigned to the physical beams, and thus the direction of the tracer particles relative to the respective part-beam is known. The interruption of the second part-beam occurs in particular independently of an influence on the first part-beam and/or the interruption of the first part-beam occurs in particular independently of an influence on the second part-beam. In other words, the first part-beam is not interrupted during the detection of the Doppler-shifted second part-beam scattered light signal, and vice versa. During the detection of the solid angle scattered light signal, the first and the second part-beams may be uninterrupted, i.e. both part-beams may impinge on the superimposition region. In particular, the method comprises several cycles. The following steps a), b) and/or c) are performed repeatedly:
detecting the Doppler-shifted solid angle scattered light signal while the first and the second part-beams are radiating onto the superimposition volume;
b) detecting the Doppler-shifted first part-beam scattered light signal while the first part-beam is radiating onto the superimposition volume and the second part-beam is interrupted;
c) detecting the Doppler-shifted second part-beam scattered light signal while the first part-beam is interrupted and the second part-beam is radiating onto the superimposition volume. Any order may be provided. Each of steps a), b) and c) is preferably repeated. Thus, at least one of the speed components or the total speed can be determined for a large number of tracer particles. In the swarm, the tracer particles comprise substantially the same speed information as the stream, so that the speed information of the stream can be determined very accurately. Preferably, a light beam or first and second part-beams with the same wavelength are used in all of steps a), b) and c).

In a preferred embodiment, the method further comprises:
providing a third part-beam (wherein in particular the light beam is further divided into a third part-beam);
directing the third part-beam along a third optical path onto the superimposition region so that the third optical path crosses the first optical path and the second optical path in the superimposition region, wherein the path into which the detected Doppler-shifted solid angle scattered light signal has been scattered is furthermore different from the third optical path.

Thus, all three speed components of the stream can be determined. The preferred variants described in relation to the first and/or second part-beam or the respective part-beam scattered light signal can also be provided for the third part-beam or a third part-beam scattered light signal. The first, second and third part-beams preferably have the same wavelength, especially when incident on the superimposition region. Preferably, the path of the solid angle scattered light signal lies substantially within a cone spanned by the first, second, and optionally third optical path (starting from the superimposition region), wherein in particular the tip of the cone is formed by the superimposition region. By determining the solid angle scattered light signal as well as the three part-beam scattered light signals, the stream can be fully characterised and all speed components as well as the total speed can be detected.

Advantageously, the method further comprises:
interrupting the third part-beam during detection of the Doppler-shifted first part-beam scattered light signal;
optionally interrupting the third part-beam during detection of the Doppler-shifted second part-beam scattered light signal.

This makes it easy to determine from which part-beam the respective part-beam scattered light signal originates.

Preferably, the method further comprises:
interrupting the third part-beam during detection of the Doppler-shifted solid angle scattered light signal.

Thus, the measurement of the Doppler-shifted solid angle scattered light signal can be performed while only the first and the second part-beams are incident on the superimposition region, and the total speed can be determined in a simple way. Alternatively or additionally, the first or the second part-beam may be interrupted during the detection of the Doppler-shifted solid angle scattered light signal. Preferably, during the detection of a respective Doppler-shifted part-beam scattered light signal, only one part-beam is interrupted at a time, i.e. during the detection of the first and second part-beam scattered light signals, the third part-beam is interrupted, etc. In this way, the measurement cycle can be shortened. It is to be expected that the different part-beam scattered light signals have different frequencies, since the tracer particles in the fluid stream do not usually move at the same speed in all directions. Therefore, simultaneous detection and evaluation of the part-beam scattered light signals is possible. Under certain circumstances, the information about which frequency corresponds to which coordinate/ which part-beam is missing—this information can be obtained by covering a part-beam.

It is advantageous if the method further comprises:

detecting a Doppler-shifted third part-beam scattered light signal, which was back-scattered by the tracer particles in the superimposition region, at least partially following the third optical path;

optionally interrupting the first part-beam and/or the second part-beam during detection of the third part-beam scattered light signal.

Preferably, the following steps are performed repeatedly:

detecting the Doppler-shifted solid angle scattered light signal while the first and second part-beams are radiating onto the superimposition volume and the third part-beam is interrupted;

b) detecting the Doppler-shifted first and preferably second part-beam scattered light signal while the first and second part-beams are radiating onto the superimposition volume and the third part-beam is interrupted;

c) detecting the Doppler-shifted second and third part-beam scattered light signal while the first part-beam is interrupted and the second and third part-beams are radiating onto the superimposition volume;

d) and optionally: detecting the Doppler-shifted first and third part-beam scattered light signals while the second part-beam is interrupted and the first and third part-beams are radiating onto the superimposition volume. Any order may be provided. Each of the steps a), b), c) and preferably d) is preferably repeated. Preferably, the steps are performed in the same order in each cycle, for example always in the order a), then b), then c), then d) (and then again from the beginning). Preferably, a light beam or first and second part-beams with the same wavelength are used in all steps a), b), c) and d), i.e. the frequency of the respective beams is not modulated.

It is advantageous if the method further comprises the following:

the detection of the first part-beam scattered light signal comprises determining an amplitude of the first part-beam scattered light signal;

preferably the detection of the second part-beam scattered light signal comprises determining an amplitude of the second part-beam scattered light signal;

preferably the detection of the third part-beam scattered light signal comprises determining an amplitude of the third part-beam scattered light signal.

It is advantageous if an angle at which the first part-beam and the second part-beam intersect in the superimposition region is different from an angle at which the second part-beam and the third part-beam intersect in the superimposition region, and preferably the angle at which the first part-beam and the third part-beam intersect in the superimposition region is different from an angle at which the first part-beam and the second part-beam intersect in the superimposition region, and preferably the angle at which the second part-beam and the third part-beam intersect in the superimposition region is different from the angle at which the first part-beam and the third part-beam intersect in the superimposition region. With the different angles, the part-beam scattered light signals can be separated, as this leads to different signals at the same speed. The more the angles differ from each other, the more the frequency of the individual signals differs and the better they can be displayed individually. This is primarily so that if the part-speeds are very similar, the signals can be reliably distinguished from each other.

It is advantageous if the method further comprises:

determining the absolute direction of movement of the fluid stream in the superimposition region at least from the amplitude of the first part-beam scattered light signal, preferably from the amplitude of the second part-beam scattered light signal and preferably from the amplitude of the third part-beam scattered light signal.

The direction of movement of the fluid per coordinate is determined by the amplitude height: if no part-beam is covered, all three amplitudes of the corresponding part-beam scattered light signals are obtained with approximately the same amplitude height. (This equal distribution of the amplitude heights depends on the beam conditioning of the part-beams—if, for example, a part-beam should be more intensive due to the choice of a certain beam splitter (cf. beam splitter 104, FIG. 1 below) (for example an 80:20 beam splitter instead of a 50:50 beam splitter), the amplitudes of the part-beam scattered light signals will no longer be equal). These amplitude heights serve as a reference. If the first part-beam is covered, an amplitude higher than the corresponding reference amplitude is obtained for the corresponding coordinate in the direction towards the beam source and an amplitude lower than the corresponding reference amplitude is obtained in the direction away from the beam source. If there is no change of direction in the coordinate axis, the amplitude is the same as the reference amplitude. This behaviour is the same for all part-beam scattered light signals, whereby the direction of movement of the corresponding coordinate can be determined depending on the covered beam.

The methods known in the prior art do not provide for a dedicated extraction of (spectrally processed) light for analysis purposes. It is therefore a further object of the invention to provide light for analysis purposes. For this purpose, it is advantageous if the method further comprises:

splitting, in particular with a filter element, a solid angle scattered light signal scattered in the path different from the first optical path, from the second optical path and optionally from the third optical path into a Doppler-shifted solid angle scattered light signal comprising the Doppler-shifted portion of the solid angle scattered light signal and an analysis scattered light signal. The analysis scattered light that has been purified from the laser spectrum or Doppler-shifted component can be used in particular for further analyses, such as temperature determination, fluorescence and/or Raman spectroscopy. Thus, for example, the chemical composition of the fluid stream can also be determined. Preferably, the solid angle scattered light signal is (in particular collimated and) directed onto the filter element by the optical element. During splitting, for example, the analysis scatter signal is transmitted by the filter element and the Doppler-shifted solid angle scattered light signal is reflected by the filter element for detection. Furthermore, in order to determine a particle concentration of the fluid stream, the intensity, in particular the amplitude, of the Doppler-shifted solid angle scattered light signal, of the analysis scattered light signal, of the first, of the second and/or of the third part-beam scattered light signal can be measured. For this purpose, a calibration can be carried out first. Advantageously, the first, the second and preferably the third optical path do not run through the filter element. The excitation light beam can be very strong compared to other signals, such as the Raman spectrum, and, when passing through lenses for example, would generate new signals, for example Raman signals of the lenses, which can superimpose the spectra of interest for analytical spectroscopy, such as for Raman or fluorescence spectroscopy. Advantageously, only the optical element, for example a converging lens, is used to focus the scattered light, in particular the part-beam scattered light signals and the solid angle scattered light signal, and the Doppler-shifted solid angle scattered light signal is reflected by the filter element and all other light frequencies are transmitted. Advantageously, the analysis scattered light signal is provided without interference from lenses.

Advantageously, the method further comprises:

determining a spectrum or characteristic value of the fluid stream from the analysis scattered light signal, for example a Raman spectrum or a fluorescence spectrum. As another example, the temperature can be determined. In particular, information about the chemical species contained can be obtained from the Raman spectrum.

The method comprises in particular the step of:

using a shutter system to unambiguously assign the detected part-beam scattered light signals and to generate multiple, serial two-beam laser Doppler systems at the solid angle detector.

The first and the second and the third part-beams preferably comprise the same frequency, in particular when incident on the superimposition region, and are preferably coherent. Preferably, providing at least a first part-beam and a second part-beam and a third part-beam comprises: providing a light beam; and splitting the light beam into at least the first part-beam and the second part-beam, in particular with a first beam splitter; splitting the first part-beam into at least the first part-beam and the third part-beam, in particular with a second beam splitter.

In particular the first part-beam and the third part-beam form an angle between each other when they enter the superimposition volume. In particular the second part-beam and the third part-beam form an angle between each other when they enter the superimposition volume.

The solid angle is preferably at least partially between the first and second and third optical paths when these meet the superimposition region. 05 can also be the angle between the first and third part-beams or between the second and third part-beams can also be the wavelength of the third part-beam.

It is advantageous if the method further comprises:

determining a third speed component of the fluid stream in the superimposition region from the second part-beam scattered light signal;

determining a third direction of movement of the third speed component of the fluid stream in the superimposition region from the third speed component and the total speed component.

It is preferred if the first part-beam scattered light signal and the second part-beam scattered light signal and the third part-beam scattered light signal are detected (at least) by the same detector.

In a preferred embodiment, the first part-beam scattered light signal and the second part-beam scattered light signal and preferably the third part-beam scattered light signal are detected using the self-mixing effect, i.e. by means of self-mixing interferometry. In particular, the first part-beam scattered light signal and the second part-beam scattered light signal and the third part-beam scattered light signal are fed back into the light source, in particular a laser cavity of the light source, wherein it interferes with the internal optical field of the light source, and is detected.

It is advantageous if the first part-beam scattered light signal for detection is derived from the first optical path and is detected by a first part-beam detector, and preferably the second part-beam scattered light signal for detection is derived from the second optical path and is detected by a second part-beam detector, and preferably the third part-beam scattered light signal for detection is derived from the third optical path and is detected by a third part-beam detector.

It is preferred if the first part-beam and the second part-beam and the third part-beam are focused on the superimposition region with an optical element (so that the first optical path and the second optical path and the third optical path intersect in the superimposition region) and the Doppler-shifted solid angle scattered light signal collimates with the same optical element.

In an advantageous variant, the method further comprises:

interrupting the first part-beam during detection of the Doppler-shifted second and third part-beam scattered light signals;

interrupting the second part-beam during detection of the Doppler-shifted first and third part-beam scattered light signals;

interrupting the third part-beam during detection of the Doppler-shifted first and second part-beam scattered light signals.

The interruption of the second part-beam occurs in particular independently of an influence on the first and third part-beams, and the interruption of the first part-beam occurs in particular independently of an influence on the second and third part-beams, and the interruption of the third part-beam occurs in particular independently of an influence on the first and second part-beams. In other words, the first part-beam is interrupted during detection of the Doppler-shifted second and third part-beam scattered light signal, etc. During the detection of the solid angle scattered light signal, the first or the second or the third part-beam may be uninterrupted, i.e. two part-beams may impinge on the superimposition region. In particular, the method comprises several cycles. The following steps a) to f) are carried out repeatedly:

detecting the Doppler-shifted solid angle scattered light signal while the first and the second part-beams are irradiating the superimposition volume, while the third part-beam is interrupted;

b) detecting the Doppler-shifted first and second part-beam scattered light signal while the first and second part-beams are irradiating the superimposition volume and the third part-beam is interrupted;

c) detecting the Doppler-shifted solid angle scattered light signal while the third and second part-beams are radiating onto the superimposition volume and the first part-beam is interrupted;

d) detecting the Doppler-shifted third and second part-beam scattered light signals while the third and second part-beams are radiating onto the superimposition volume and the first part-beam is interrupted;

e) detecting the Doppler-shifted solid angle scattered light signal while the third and first part-beams are radiating onto the superimposition volume and the second part-beam is interrupted;

f) detecting the Doppler-shifted third and first part-beam scattered light signal while the third and first part-beams are radiating onto the superimposition volume and the second part-beam is interrupted.

Advantageously, the method comprises a step for determining the absolute direction of movement by evaluating the amplitudes of the scattered light signals at the solid angle detector, wherein the angles of the first, second and third part-beams are different from each other and one of each of the first, second and third part-beams is alternately blocked.

With reference to the device according to the invention, it is advantageous if the light source arrangement is intended for providing a third part-beam; and the optical directing device is intended for directing the third part-beam along a third optical path onto the superimposition region so that the third optical path crosses the first optical path and the second optical path in the superimposition region, wherein the path into which the detected Doppler-shifted solid angle scattered light signal has been scattered is furthermore different from the third optical path.

Preferably, the device, in particular the light source arrangement, comprises a second beam splitter with which the third part-beam is (further) split off from the light beam, from the first part-beam and/or from the second part-beam. The third optical path is in particular partially different from the first and the second optical path. Preferably, the same angle lies between the first and the second part-beam, between the second and the third part-beam, and between the third and the first part-beam when they impinge on the superimposition region.

In a preferred embodiment, the device comprises:

an optical element with which the first part-beam, the second part-beam and optionally the third part-beam are cross-focused onto the superimposition region and with which the Doppler-shifted solid angle scattered light signal is focused. Thus, a single receiving and transmitting optic may be sufficient. Preferably, the first, the second and/or the third part-beam scattered light signal are also focused or directed along the respective optical path by the optical element. The optical element is preferably a lens, in particular a converging lens.

It is preferred if the device comprises a filter element with which a solid angle scattered light signal scattered along the path different from the first, second and preferably third optical path is split into a Doppler-shifted solid angle scattered light signal, comprising the Doppler-shifted portion of the solid angle scattered light signal, and an analysis scattered light signal. Preferably, the filter element is arranged at least partially between the first, second and preferably third part-beams Preferably, a converging lens is provided, with which the Doppler-shifted solid angle scattered light signal is focused onto a detector after the filter element.

It is advantageous if the first part-beam, the second part-beam and optionally the third part-beam run past the filter element. In other words, it is advantageous if the first part-beam, the second part-beam and the third part-beam are not filtered or influenced by the filter element. Preferably, the first, second and third part-beam scattered light signals are detected unfiltered.

In a preferred embodiment, the device comprises:

a first shutter, with which the first part-beam can be interrupted (in particular independently of the other part-beams);

optionally a second shutter, with which the second part-beam can be interrupted (in particular independently of the other part-beams);

optionally a third shutter, with which the third part-beam can be interrupted (in particular independently of the other part-beams) The first shutter is preferably located in the first optical path at a point where the first optical path differs from the second and preferably third optical path. The second shutter is preferably arranged in the second optical path at a location where the second optical path differs from the first and preferably third optical path. The third shutter is preferably arranged in the third optical path at a location where the third optical path differs from the first and preferably second optical path. In other words, the first shutter is preferably arranged in the first optical path, but not in the second and third optical paths. The second shutter is preferably arranged in the second optical path, but not in the first and third optical paths. The third shutter is preferably arranged in the third optical path, but not in the first and second optical paths. With the shutters, the optical paths can thus be blocked individually and the assignment of excitation beam and frequency is simplified.

Preferably, the device comprises a further beam splitter which is arranged in the beam path of the light beam between the light source and the first beam splitter. With the further beam splitter, the first, and preferably the second and/or third part-beam scattered light signal is fed to the part-beam detector. Thus, all part-beam scattered light signals can be detected with a single detector.

Advantageously, the device comprises at least one further first beam splitter in the first optical path to guide the first part-beam scattered light signal to a first part-beam scattered light detector. Preferably, the device comprises a further second beam splitter in the second optical path to guide the second part-beam scattered light signal to a second part-beam scattered light detector. Preferably, the device comprises a further third beam splitter in the third optical path to guide the third part-beam scattered light signal to a third part-beam scattered light detector.

Furthermore, the light source arrangement preferably comprises a light source for providing a light beam and a second beam splitter for splitting the light beam into the first part-beam and the third part-beam. In particular, the first optical path and the second optical path each extend from the first beam splitter to the superimposition region, and the first optical path and the third optical path each extend from the second beam splitter to the superimposition region. Preferably, the first optical path and the second optical path and the third optical path are different outside the superimposition region. In particular, the first optical path is partially different from the second optical path and from the third optical path.

BRIEF DESCRIPTION OF THE DRAWINGS

The invention is explained in greater detail below with reference to preferred embodiments shown in the figures.

DESCRIPTION OF EXAMPLE EMBODIMENTS

Figure 1:
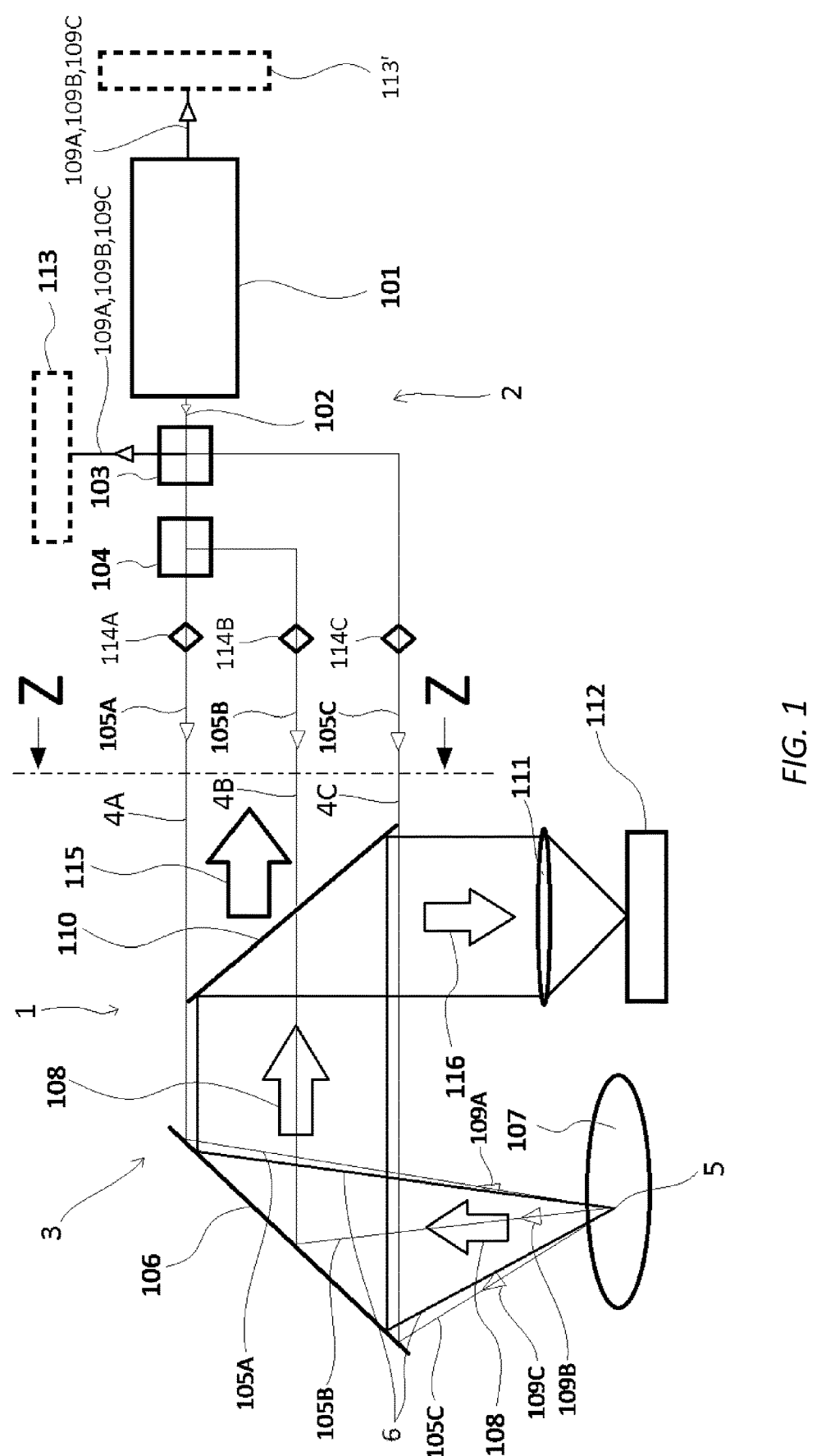
FIG. 1 schematically shows a preferred embodiment of the device according to the invention.
Figure 2:
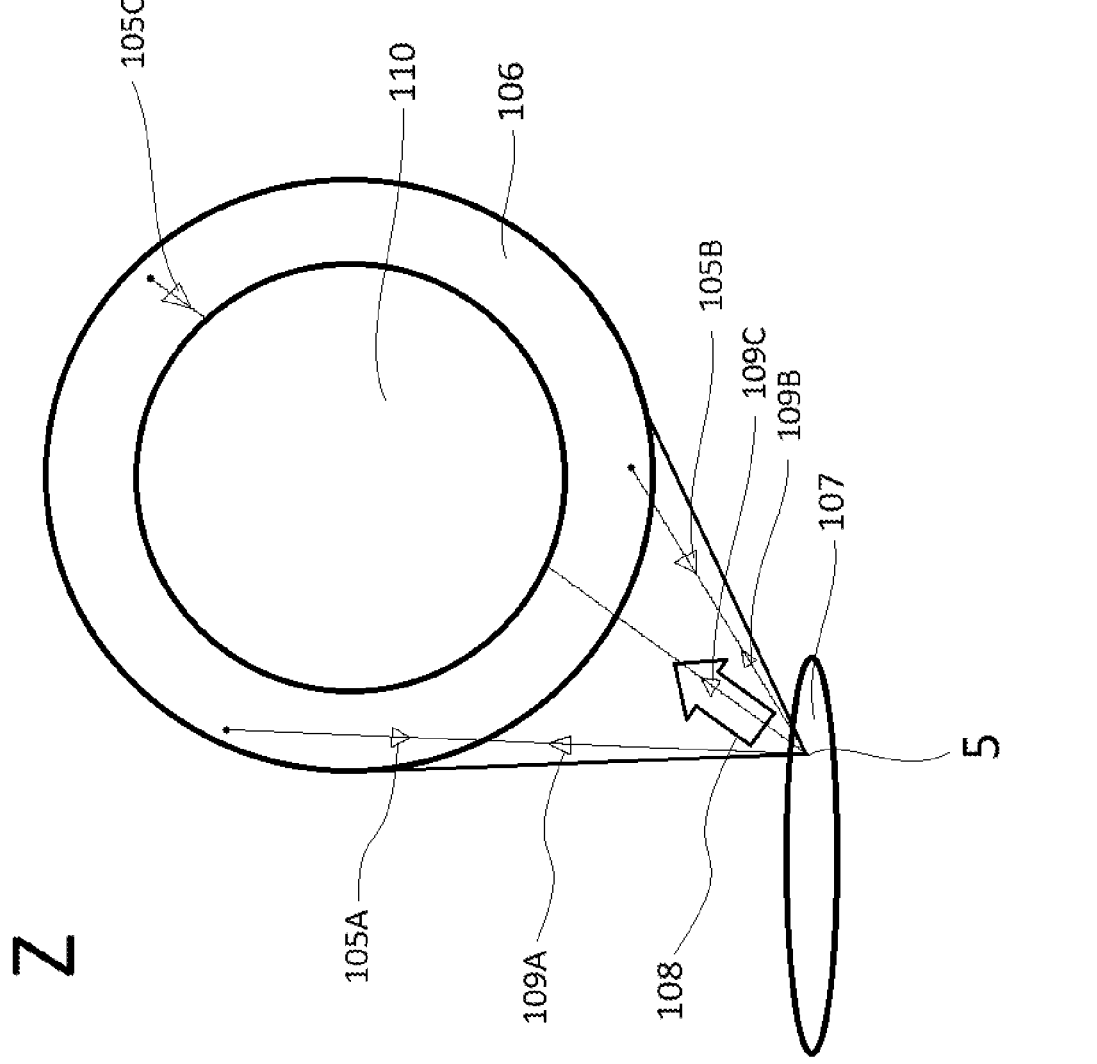
FIG. 2 schematically shows a detail of the same device as FIG. 1 from a different perspective.

FIG. 1 schematically shows a preferred embodiment of the device 1 for determining at least one speed component of a fluid stream, in particular for laser Doppler anemometry. FIG. 2 shows a detail of the same embodiment of the device 1 as FIG. 1 from a different perspective, substantially in a section from the direction Z marked with an arrow. The device 1 comprises a light source arrangement 2 for providing a first part-beam 105A, a second part-beam 105B and a third part-beam 105C. The light source arrangement comprises a light source 101, in particular a laser, which emits a light beam 102. A first beam splitter 104 and a second beam splitter 103 split the light beam into the first part-beam 105A, the second part-beam 105B and the third part-beam 105C.

With an optical directing device 3, the first part-beam 105A is directed along a first optical path 4A, the second part-beam 105B is directed along a second optical path 4B, and the third part-beam 105C is directed along a third optical path 4C to a superimposition region 5 within the fluid stream so that the first optical path 4A, the second optical path 4B, and the third optical path 4C intersect in the superimposition region. Similarly, the first part-beam 105A, the second part-beam 105B and the third part-beam 105C intersect in the superimposition region 5 (provided that the respective part-beams 105A, 105B, 105C are not interrupted). In order to focus the first, second and third part-beams 105A, 105B, 105C on the superimposition region 5, the directing device 3 comprises an optical element 106, in particular a mirror.

In the first optical path 4A, a first shutter 114A is provided for interrupting the first part-beam 105A, in the second optical path 4B, a second shutter 114B is provided for interrupting the second part-beam 105B, and in the third optical path 4C, a third shutter 114C is provided for interrupting the third part-beam 105C.

Tracer particles 107 are provided in the fluid stream. The first part-beam 105A, second part-beam 105B and third part-beam 105C (or a subset of the three part-beams 105A, 105B, 105C if one or more of the part-beams 105A, 105B, 105C is/are interrupted by the respective shutter 114A, 114B, 114C) encountering a tracer particle 107 in the superimposition region 5 are at least partially scattered by the tracer particle 107 as a scattered light signal. A portion of the scattered light signal follows the first optical path 4A as a first part-beam scattered light signal 109A, a portion follows the second optical path 4B as a second part-beam scattered light signal 109B, and a portion follows the third optical path 4C as a third part-beam scattered light signal 109C. Furthermore, a portion of the scattered light is scattered as a solid angle scattered light signal 108 along a path 6 different from the first, second and third optical paths 105A, 105B, 105C. The path 6 lies substantially within a cone spanned by the first, second and third optical paths 105A, 105B, 105C, wherein the superimposition region 5 lies at the apex of the cone.

The first, second and third part-beam scattered light signals 109A, 109B, 109C follow the respective first, second and third optical paths 4A, 4B, 4C back via the optical element 106. In the process, the first part-beam scattered light signal 109A and the second part-beam scattered light signal 109B are combined by the first beam splitter 104 on an optical path. From the second beam splitter 103, the first and/or second and/or third part-beam scattered light signal 109A, 109B, 109C (depending on whether one of the optical paths 4A, 4B, 4C is interrupted) can be guided to the part-beam detector 113 and detected by it. Additionally or alternatively, the first and/or second and/or third part-beam scattered light signal 109A, 109B, 109C are guided into the light source 101 and subsequently detected by the part-beam detector 113' utilising the self-mixing effect.

Thus, the part-beam detector(s) 113, 113' is/are arranged to detect the Doppler-shifted first part-beam scattered light signal 109A, the Doppler-shifted second part-beam scattered light signal 109B, and the Doppler-shifted third part-beam scattered light signal 109C, which have been back-scattered by tracer particles 107 in the superimposition region 5, following (along) the respective optical path 4A, 4B, 4C.

The solid angle scattered light signal 108 is collimated by the optical element 106 and directed towards the filter element 110. As can be seen in particular in FIG. 2, the first, second and third part-beams 105A, 105B, 105C bypass the filter element 110. The filter element 110 splits the solid angle scattered light signal 108 into a Doppler-shifted solid angle scattered light signal 116 and an analysis scattered light signal 115. Specifically, the filter element 110 reflects the Doppler-shifted portion of the solid angle scattered light signal 108 and directs the Doppler-shifted solid angle scattered light signal 116 to a converging lens 111, which focuses the Doppler-shifted solid angle scattered light signal 116 onto a solid angle detector 112. Furthermore, the filter element 110 transmits the analysis scattered light 115, which represents the portion of the solid angle scattered light signal 108 that has been cleaned from the laser spectrum. The analysis scattered light 115 can be used for further analyses, for example temperature measurement, Raman or fluorescence spectroscopy.

The solid angle detector 112 is thus arranged to detect the Doppler-shifted solid angle scattered light signal 116 scattered by the tracer particles 107 in the superimposition region 5 into the path 6 different from the first, second and third optical paths 4A, 4B, 4C.

Figure 3:
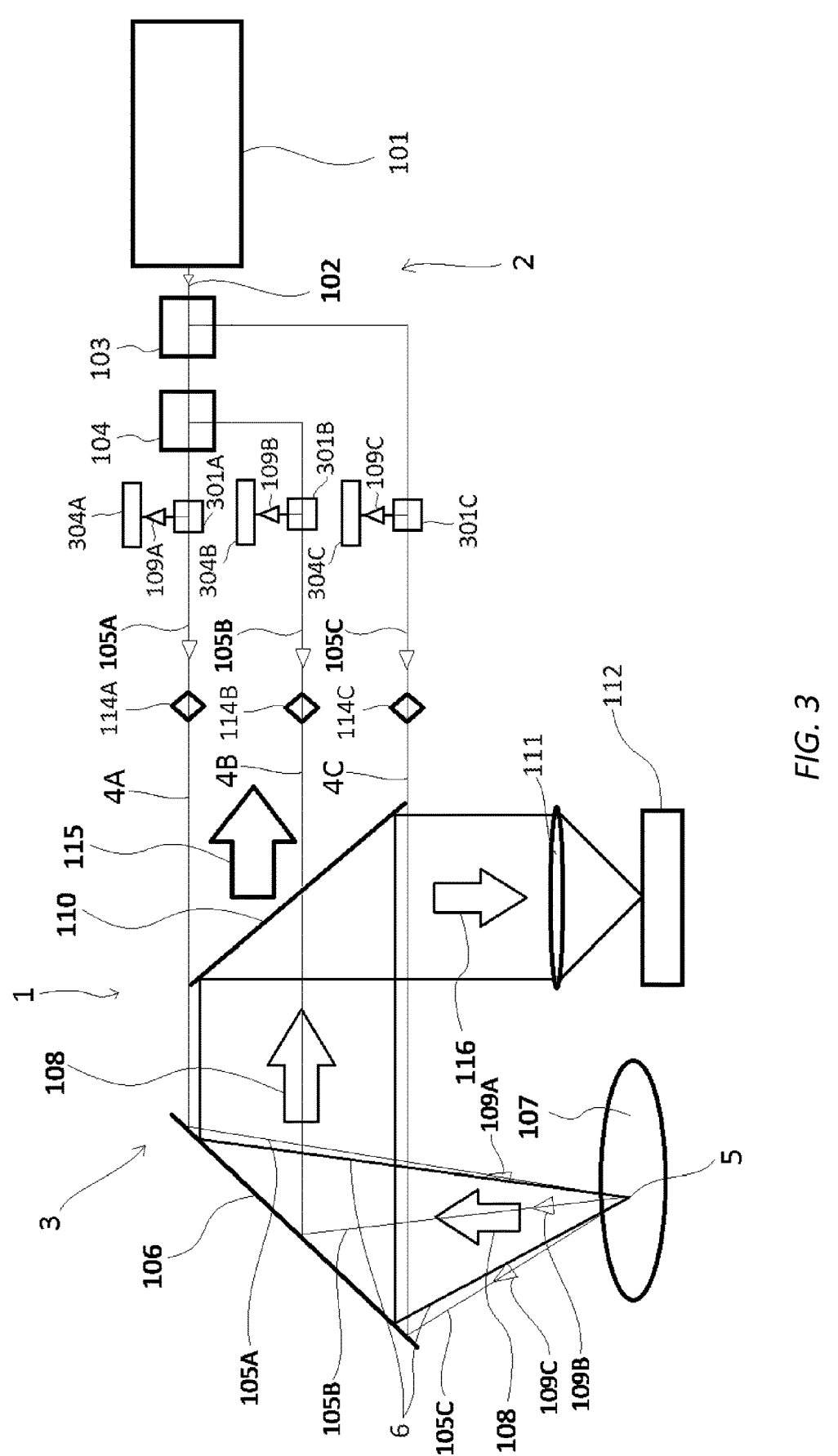
FIG. 3 schematically shows a further preferred embodiment of the device according to the invention.

FIG. 3 shows a further preferred embodiment of the device 1. The embodiment differs from that shown in FIG. 1 mainly in the arrangement of the part-beam detectors. In the first optical path 4A, a first detector beam splitter 301A is provided between the first and the second beam splitter 104, 103 and the superimposition region 5, in particular between the first and the second beam splitter 104, 103 and the first shutter 114A. With the first detector beam splitter 301A, the first part-beam scattered light signal 109A is guided to a first part-beam detector 304A, with which the first (Doppler-shifted) part-beam scattered light signal 109A is detected. In the second optical path 4B, a second detector beam splitter 301B is provided between the first and second beam splitters 104, 103 and the superimposition region 5, in particular between the first and second beam splitters 104, 103 and the second shutter 114B. With the second detector beam splitter 301B, the second part-beam scattered light signal 109B is guided to a second part-beam detector 304B, with which the second part-beam scattered light signal 109B is detected. In the third optical path 4C, a third detector beam splitter 301C is provided between the second beam splitter 103 and the superimposition region 5, in particular between the second beam splitter 103 and the third shutter 114C. With the third detector beam splitter 301C, the third part-beam scattered light signal 109C is guided to a third part-beam detector 304C, with which the third part-beam scattered light signal 109C is detected. Thus, the three part-beam scattered light signals 109A, 109B, 109C can each be detected with a separate part-beam detector 304A, 304B, 304C.

Figure 4:
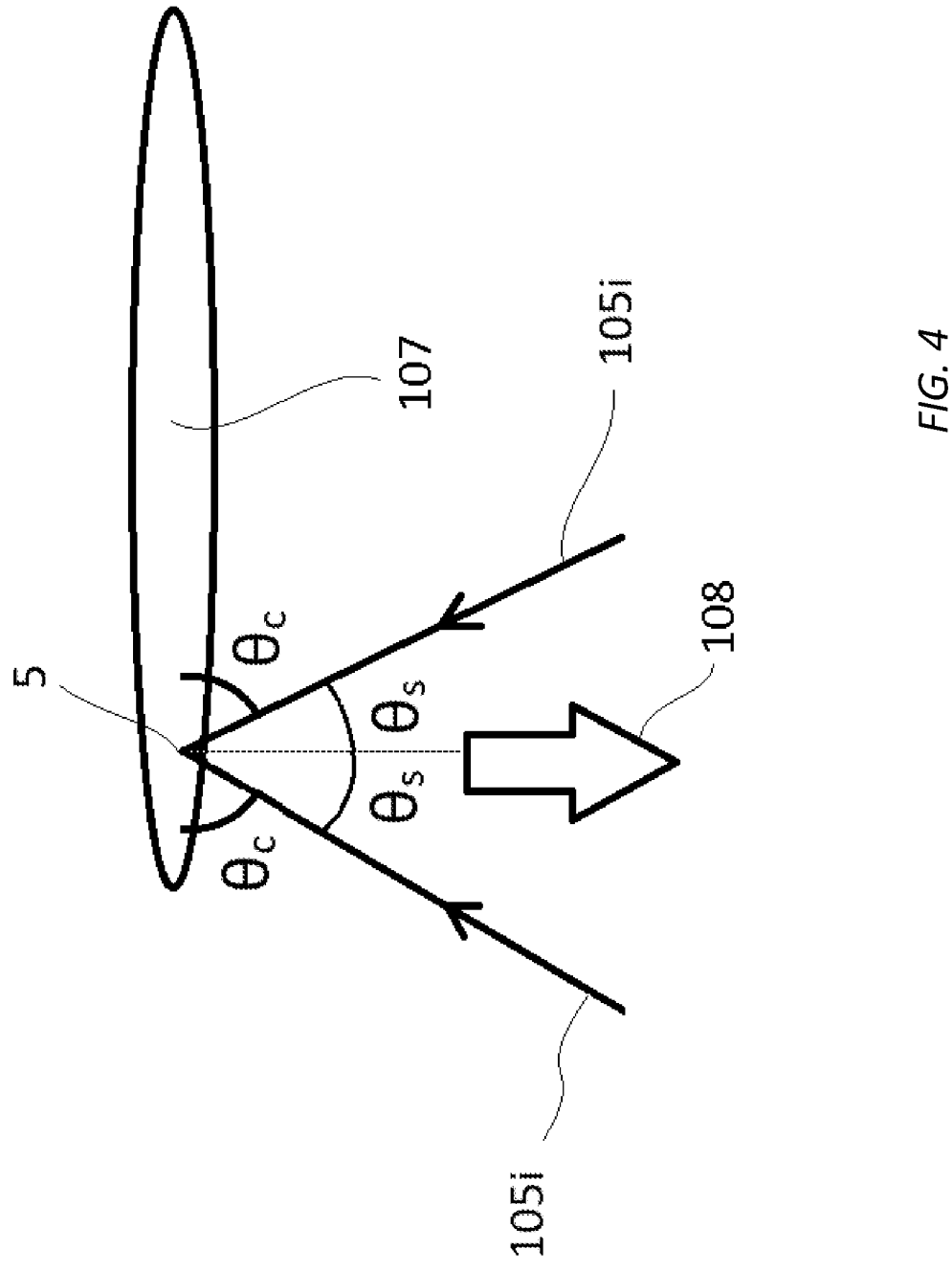
FIG. 4 schematically illustrates the evaluation of the Doppler-shifted solid angle scattered light signal with formed angle between two part-beams $\theta_s$ and with angle between part-beams and coordinate axis $\theta_c$.
Figure 5:
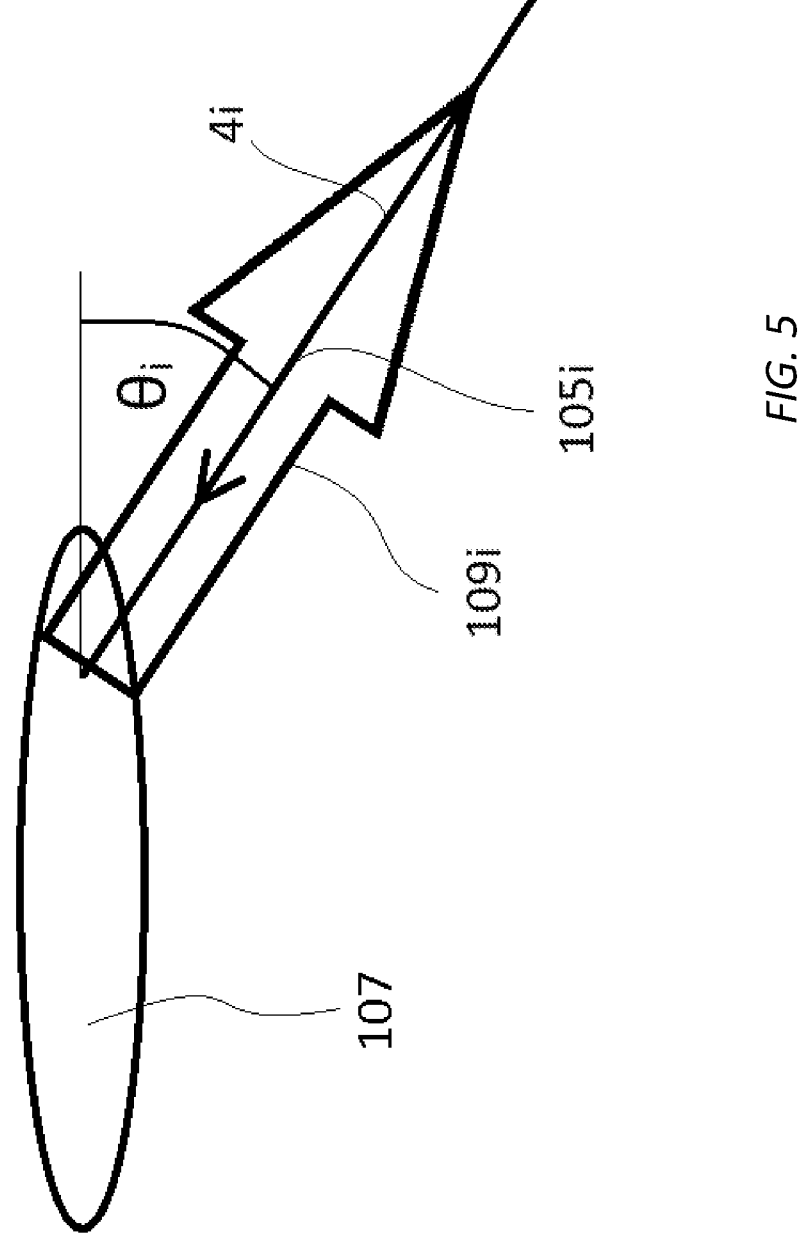
FIG. 5 schematically illustrates the evaluation of the Doppler-shifted part-beam scattered light signal with the angular dependence on the coordinate axis $\theta_i$.

FIGS. 4 and 5 illustrate the evaluation of the Doppler-shifted scattered light signals. In particular, FIG. 4 illustrates the evaluation of the Doppler-shifted solid angle scattered light signal 116 and the determination of the total speed. In the embodiment shown, either only two part-beams 105i, namely the first part-beam 105A and the second part-beam 105B, or the first part-beam 105A and the third part-beam 105C, or the second part-beam 105B and the third part-beam 105C are provided, or three part-beams are provided, one of the part-beams, for example the third part-beam 105C, being interrupted for the determination of the total speed. A portion of the scattered light signal scattered by the tracer particles 107 in the superimposition region 5 is scattered in the space/path 6 as a solid angle scattered light signal 108. As explained in conjunction with FIGS. 1 to 3, the Doppler-shifted solid angle scattered light signal 116, which is substantially the Doppler-shifted portion of the solid angle scattered light signal 108, is subsequently detected by the detector 112.

By detecting the Doppler-shifted solid angle scattering signal 116, the total speed V can be determined using formula (4)

$$V = \frac{f_d \lambda}{2\sin\theta_s} \quad (4)$$

wherein $\theta_s$ is the angle between the first part-beam and the optical axis (incidence angle) and is the wavelength of the first part-beam. $f_d$ is the frequency of the Doppler-shifted solid angle scattered light signal 116 which frequency is measured at the solid angle detector 112. Alternatively, the total speed V can be determined using formula (5)

$$V = \frac{f_d \lambda}{2\cos\theta_c} \quad (5)$$

wherein $\theta_c$ is the angle of incidence between the first part-beam 105A or the second part-beam 105B or the third part-beam 105C and a coordinate axis.

FIG. 5 illustrates the evaluation of the Doppler-shifted part-beam scattered light signals 105A, 105B, 105C. One of the part-beams 105A, 105B, 105C, wherein the respective part-beam is labelled 105i in FIG. 5, is incident on the tracer particle 107 in FIG. 5. The other two of the part-beams 105A, 105B, 105C may be interrupted during this time. The part-beam 105i impinges on the tracer particle 107 at an angle $\theta_i$ relative to the coordinate axis. The respective part-beam scattered light signal 109i (i.e. the respective one of the part-beam scattered light signals 109A, 109B, 109C) back-scattered along the optical path 4i of the part-beam 105i is detected by the part-beam detector, wherein one (or more) part-beam detectors 113, 113' may be provided, which can detect the part-beam scattered light signals 109A, 109B, 109C of all optical paths 4A, 4B, 4C, and/or a first, second and third part-beam detector 304A, 304B, 304C respectively assigned to one of the optical paths 4A, 4B, 4C can detect the respective part-beam scattered light signal 109i. The respective speed component can be calculated by means of formula (6)

$$v_i = \frac{f_i \lambda}{2} = V\cos\theta_i \quad (6)$$

with the angle of movement $\theta_i$ (formula (7))

$$\theta_i = \cos^{-1}\frac{f_i \lambda}{2V} \quad (7)$$

between the coordinate axis and the direction of movement of the tracer particle 107. Here, $f_i$ is the frequency of the respective Doppler-shifted part-beam scattered light signal 109i. By alternately blocking the individual part-beams 105A, 105B, 105C, the directions of movement relative to a respective part-beam 105i can be determined. This also results in a clear assignment between frequency and part-beam if only one part-beam is blocked at a time.

Figure 6:
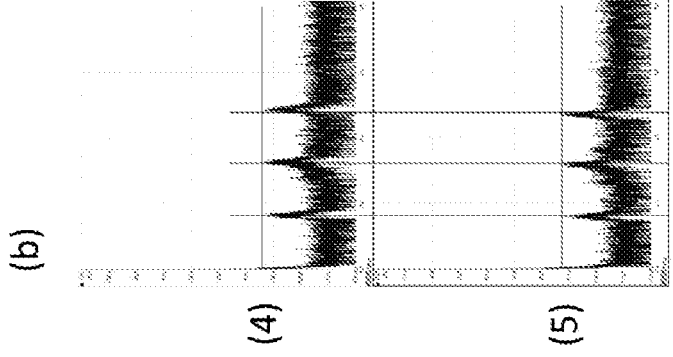
FIG. 6 shows under (b) a measured scattered light signal at a detector with different angles of incidence $(\theta_{s1}, \theta_{s2}, \theta_{s3})$ and under (a) with partially covered excitation beams.
Figure 6:
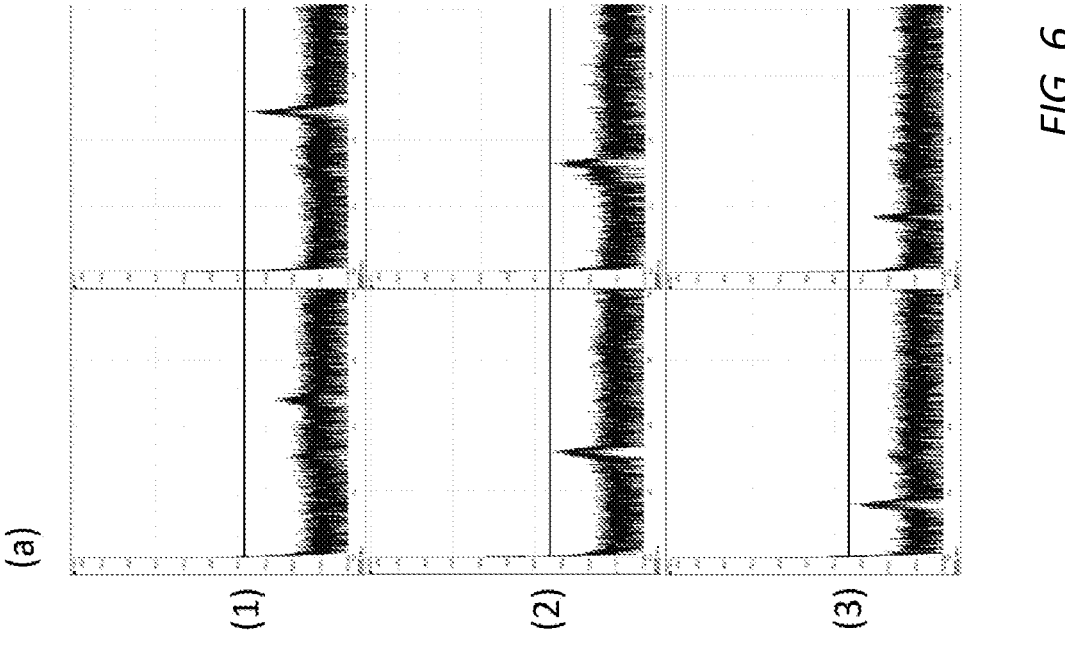

FIG. 6 shows the measured scattered light signal at the solid angle detector 112, wherein the angles $\theta_{s1}$, $\theta_{s2}$, $\theta_{s3}$ of the excitation beams are different from each other. This results in three different and thus distinguishable frequencies. The amplitude information under (b) contains the particle concentration (wherein calibration may be necessary), but no directional information. Graphs (4) and (5) show the signals of a rotating disc in clockwise and anti-clockwise direction, wherein the speed was the same in both directions. If a part-beam 105i is now covered, not only the general coordinate movement (x, y, z) can be determined but also the direction of movement along the coordinate can be determined via the amplitude height (FIG. 6 (a) left: anti-clockwise rotation, FIG. 6 (a) right: clockwise rotation). Graph (1) and graph (3) show the clockwise and anti-clockwise movement of a rotating disc, graph (2) shows the movement in the direction normal to the measurement apparatus, which did not change. The speed is calculated as already described; the direction can be determined via the amplitude height (wherein calibration may be necessary).

The detected signals can be evaluated in several ways. In addition to the methods already described, information can also be obtained from the signal amplitude.

By using different angles $\theta_s$ ($\theta_{s1}$, $\theta_{s2}$, $\theta_{s3}$) between the part-beams 105A, 105B, 105C, three different signals with different frequencies are obtained at the solid angle detector 112 (cf. FIG. 6*b*). When covering one part-beam, only one signal with one frequency is detected at the solid angle detector 112 (cf. FIG. 6*a*). The amplitude of this signal, which amplitude is proportional to the scattered light intensity (depending, among other things, on the particle concentration), varies depending on the direction (cf. FIG. 6*a*). If the angles $\theta_s$ between the part-beams 105A, 105B, 105C are the same, only a signal with a frequency is obtained at the solid angle detector 112, with which only the information of the particle quantity is contained in the amplitude. However, calibration may be necessary to evaluate this information.

As described above, amplitude heights without interruption of a part-beam serve as a reference. If, for example, the first part-beam is covered, an amplitude higher than the corresponding reference amplitude is obtained for the corresponding coordinate for the movement of the fluid/tracer particle in the direction towards the beam source and an amplitude lower than the corresponding reference amplitude in the direction away from the beam source. As can be seen in FIG. 6, only a slight increase occurs; in contrast, the attenuation is much more pronounced (in FIGS. 6 (1) and (3): attenuation approximately 10 dB, increase approximately 5 dB compared to the reference amplitude—note: the increase in (1) correlates with reference (4) and the increase in (3) correlates with reference (5), as these are different directions of rotation—accordingly, attenuation (1) correlates with reference (5) and attenuation (3) with reference (4)).

As also described above, the amplitude is the same as the reference amplitude if there is no change of direction in the coordinate axis. This is the case with the rotating disc used in the measurement of the signals in FIG. 6: in the x- and y-axis there are pronounced amplitude changes corresponding to the direction of rotation of the disc, while the amplitude in the z-direction does not change.

The invention claimed is:

1. A method for determining at least one speed component of a fluid stream, for laser Doppler anemometry, the method comprising at least the steps of:
providing at least a first part-beam and a second part-beam;
directing the first part-beam along a first optical path and directing the second part-beam along a second optical path onto a superimposition region within the fluid stream so that the first optical path and the second optical path intersect in the superimposition region;
detecting a Doppler-shifted first part-beam scattered light signal, which was back-scattered by tracer particles in the fluid stream in the superimposition region, at least partially following the first optical path;
detecting a Doppler-shifted solid angle scattered light signal, which was scattered by the tracer particles in the superimposition region into a path different at least from the first optical path and from the second optical path,
determining a first speed component of the fluid stream in the superimposition region from the Doppler-shifted first part-beam scattered light signal;
determining a total speed of the fluid stream in the superimposition region from the Doppler-shifted solid angle scattered light signal; and
determining a first direction of movement of the first speed component of the fluid stream in the superimposition region from the first speed component and the total speed.

2. The method according to claim 1, further comprising:
detecting a Doppler-shifted second part-beam scattered light signal, which was back-scattered by the tracer particles in the superimposition region, at least partially following the second optical path;
determining a second speed component of the fluid stream in the superimposition region from the Doppler-shifted second part-beam scattered light signal;
determining a second direction of movement of the second speed component of the fluid stream in the superimposition region from the second speed component and the total speed.

3. The method according to claim 2, wherein the Doppler-shifted first part-beam scattered light signal and the Doppler-shifted second part-beam scattered light signal are detected by the same detector.

4. The method according to claim 2, wherein the Doppler-shifted first part-beam scattered light signal is led off from the first optical path for detection and is detected by a first part-beam detector, and the Doppler-shifted second part-beam scattered light signal is led off from the second optical path for detection and is detected by a second part-beam detector.

5. The method according to claim 1, wherein the first part-beam and the second part-beam are focused on the superimposition region with an optical element and the Doppler-shifted solid angle scattered light signal is collected with the same optical element.

6. The method according to claim 1, wherein the detection of the Doppler-shifted first part-beam scattered light signal and the detection of the Doppler-shifted solid angle scattered light signal comprises at least measuring the frequency of the respective scattered light signal.

7. The method according to claim 1, further comprising:
interrupting the second part-beam during detection of the Doppler-shifted first part-beam scattered light signal.

8. The method according to claim 1, further comprising:
providing a third part-beam;
directing the third part-beam along a third optical path to the superimposition region so that the third optical path crosses the first optical path and the second optical path in the superimposition region, wherein the path into which the detected Doppler-shifted solid angle scattered light signal has been scattered is furthermore different from the third optical path.

9. The method according to claim 8, further comprising:
interrupting the third part-beam during detection of the Doppler-shifted first part-beam scattered light signal.

10. The method according to claim 8, further comprising:
interrupting the third part-beam during detection of the Doppler-shifted solid angle scattered light signal.

11. The method according to claim 8, further comprising:
detecting a Doppler-shifted third part-beam scattered light signal, which was back-scattered by the tracer particles in the superimposition region, at least partially following the third optical path;
interrupting the first part-beam during detection of the third part-beam scattered light signal.

12. The method according to claim 7, wherein
the detection of the Doppler-shifted first part-beam scattered light signal comprises determining an amplitude of the first part-beam scattered light signal.

13. The method according to claim 2, wherein an angle at which the first part-beam and the second part-beam intersect in the superimposition region is different from an angle at which the second part-beam and the third part-beam intersect in the superimposition region.

14. The method according to claim 12, wherein the method comprises:

determining an absolute direction of movement of the fluid stream in the superimposition region at least from the amplitude of the first part-beam scattered light signal.

15. The method according to claim 1, further comprising:

splitting, with a filter element, a solid angle scattered light signal scattered in the path different from the first optical path and from the second optical path into the Doppler-shifted solid angle scattered light signal comprising the Doppler-shifted portion of the solid angle scattered light signal and an analysis scattered light signal.

16. The method according to claim 15, further comprising:

determining a spectrum or characteristic value of the fluid stream from the analysis scattered light signal, comprising a Raman spectrum and/or a fluorescence spectrum.

17. A device for determining at least one speed component of a fluid stream, for laser Doppler anemometry, the device comprising:

a light source arrangement for providing at least a first part-beam and a second part-beam;

an optical directing device for directing the first part-beam along a first optical path and the second part-beam along a second optical path to a superimposition region within a fluid stream so that the first optical path and the second optical path intersect in the superimposition region;

a part-beam detector arranged to detect a Doppler-shifted first part-beam scattered light signal, which was back-scattered by tracer particles in the fluid stream in the superimposition region, at least partially following the first optical path;

a solid angle detector arranged to detect a Doppler-shifted solid angle scattered light signal, which was scattered by the tracer particles in the superimposition region into a path different at least from the first optical path and from the second optical path; and a control and data acquisition unit configured for conducting the method of claim 1.

18. The device according to claim 17, wherein the light source arrangement is intended for providing a third part-beam; and the optical directing device is intended for directing the third part-beam along a third optical path to the superimposition region so that the third optical path intersects the first optical path and the second optical path in the superimposition region, wherein the path into which the detected Doppler-shifted solid angle scattered light signal has been scattered is furthermore different from the third optical path.

19. The device according to claim 17, wherein the optical directing device comprises:

an optical element with which the first part-beam and the second part-beam are cross-focused onto the superimposition region and with which the Doppler-shifted solid angle scattered light signal is focused.

20. The device according to claim 17, comprising a filter element with which a solid angle scattered light signal scattered in the path different at least from the first optical path and from the second optical path is split into the Doppler-shifted solid angle scattered light signal, comprising the Doppler-shifted portion of the solid angle scattered light signal, and an analysis scattered light signal.

21. The device according to claim 20, wherein the first part-beam and the second part-beam run past the filter element.

22. The device according to claim 17, comprising:

a first shutter, with which the first part-beam can be interrupted; and a second shutter, with which the second part-beam can be interrupted.

* * * * *